(12) United States Patent
Kavanaugh et al.

(10) Patent No.: US 7,705,117 B2
(45) Date of Patent: Apr. 27, 2010

(54) EGFH2 GENES AND GENE PRODUCTS

(75) Inventors: W. Michael Kavanaugh, Mill Valley, CA (US); Hui Cen, Oakland, CA (US); Pauline Lee, Novato, CA (US)

(73) Assignee: Chiron Corporation, Emeryville, CA (US)

( * ) Notice: Subject to any disclaimer, the term of this patent is extended or adjusted under 35 U.S.C. 154(b) by 202 days.

(21) Appl. No.: 11/656,882

(22) Filed: Jan. 22, 2007

(65) Prior Publication Data

US 2008/0004428 A1    Jan. 3, 2008

Related U.S. Application Data

(62) Division of application No. 09/640,041, filed on Aug. 15, 2000, now Pat. No. 6,825,333.

(60) Provisional application No. 60/149,986, filed on Aug. 20, 1999.

(51) Int. Cl.
*A61K 38/00* (2006.01)
*C07K 14/00* (2006.01)

(52) U.S. Cl. ..................... 530/300; 530/350

(58) Field of Classification Search .............. None
See application file for complete search history.

(56) References Cited

U.S. PATENT DOCUMENTS

| | | | |
|---|---|---|---|
| 6,335,170 | B1 | 1/2002 | Orntoft |
| 6,387,638 | B1 | 5/2002 | Ballinger et al. |
| 6,544,759 | B1 | 4/2003 | Harari et al. |
| 6,936,417 | B2 | 8/2005 | Orntoft |
| 6,949,245 | B1 | 9/2005 | Sliwkoski |
| 7,041,292 | B1 | 5/2006 | Sliwkoski |
| 2003/0086924 | A1 | 5/2003 | Sliwkowski |
| 2003/0204075 | A9 | 10/2003 | Wang |
| 2004/0013667 | A1 | 1/2004 | Kelsey et al. |
| 2004/0121326 | A1 | 6/2004 | Harari et al. |
| 2005/0208043 | A1 | 9/2005 | Adams et al. |
| 2005/0238640 | A1 | 10/2005 | Sliwkoski |
| 2006/0034842 | A1 | 2/2006 | Adams et al. |
| 2006/0073143 | A1 | 4/2006 | Adams et al. |
| 2006/0083739 | A1 | 4/2006 | Sliwkoski |
| 2006/0134682 | A1 | 6/2006 | Roberts et al. |
| 2006/0193854 | A1 | 8/2006 | Adams et al. |
| 2006/0198843 | A1 | 9/2006 | Adams et al. |
| 2006/0216285 | A1 | 9/2006 | Adams et al. |
| 2007/0009530 | A1 | 1/2007 | Altaba et al. |

FOREIGN PATENT DOCUMENTS

| | | |
|---|---|---|
| WO | WO 9805761 | 2/1998 |
| WO | WO 9918976 | 4/1999 |
| WO | WO 9965924 | 12/1999 |
| WO | WO 0052204 | 9/2000 |
| WO | WO 0100238 | 1/2001 |
| WO | WO 0100245 | 1/2001 |

OTHER PUBLICATIONS

Burgess et al., J Cell Biol. 111:2129-2138, 1990.*
Wang et al. JBC, 2001 276:49213-49220.*
Whisstock et al ., Quarterly Review of Biophysics, 2003, 36, pp. 307-340).*
GenBank Accession No. AA238077 dated Mar. 3, 1997, 2 pages.
Harari, D., et al., "Neuregulin-4: a novel growth factor that acts through the ErbB-4 receptor tyrosine kinase", Oncogene (1999) 18, pp. 2681-2689.
Starr, A., et al., "ErbB4 increases the proliferation potential of human lung cancer cells and its blockage can be used as a target for anti-cancer therapy", Cancer Cell Biology, 12 pages, 2006, v. 119 (2).
Yeda Research and Development Co., Ltd., "Neuregulin-4 (NRG4), a Novel Growth Factor Which Acts Through the Erbb4 Receptor Tyrosine Kinase; Sequences, Antibodies To and Uses Thereof." [online] [retrieved on Aug. 2006]. Retrieved from the Internet: http://www.yedarnd.com/opportunities/?id=1236&act=print.
Anderson (Nature 1998; 392(Supp); 25-30).
Lazar et al., Mol Cell Biol. 8:1247-1252, 1988.
Mikayama et al. (PNAS, 1993, 90: 10056-10060).
Ngo et al., in "The Protein Folding Problem and Tertiary Structure Prediction", 1994 (ed.), Birkhauser, Boston, MA, pp. 433 and 492-495.
Skolnick and Fetrow (Trends in Biotechnology, 2000. 18(1): 34-39).
Spitler LE (Cancer Biotherapy 1995; 10(1): 1-3).

* cited by examiner

*Primary Examiner*—Michail A Belyavskyi
(74) *Attorney, Agent, or Firm*—Lisa Alexander; McDermott Will & Emery LLP

(57) ABSTRACT

This invention relates to mouse and human EGFH2, and to variants thereof and to polynucleotides encoding EGFH2. This invention also relates to therapeutic agents related to the polynucleotides and proteins.

12 Claims, 4 Drawing Sheets

| | | |
|---|---|---|
| hEGFH2 seq | 1 MPTDHEEPCGPSHKSFCLNGGLCYVIPTIPSPFCRCVENYTGARCEEVFLP | 51 |
| mEGFH2 seq | 1 MPTDHEQPCGPRHRSFCLNGGICYVIPTIPSPFCRCIENYTGARCEEVFLP | 51 |
| | ****** **** * ******* ************** ************** | |
| hEGFH2 seq | 52 GSSIQTKSNLFEAFVALAVLVTLIIGAFYFLCRKGHFQRASSVQYDINLVE | 102 |
| mEGFH2 seq | 52 SSSIPSESNLSAAFVVLAVLLTLTIAALCFLCRKGHLQRASSVQCEISLVE | 102 |
| | ***    ***   *** **** ** * *  ******* ******  * *** | |
| hEGFH2 seq | 103 TSSTSAHHSHEQH | 115 |
| mEGFH2 seq | 103 TNNTRTRHSHREH | 115 |
| | *  *   *** * | |

*Fig. 1*

Sequence Range: 1 to 348

```
                              25                                              50
ATG CCA ACA GAT CAC GAA GAG CCC TGT GGT CCC AGT CAC AAG TCG TTT TGC
TAC GGT TGT CTA GTG CTT CTC GGG ACA CCA GGG TCA GTG TTC AGC AAA ACG 75                                              100
CTG AAT GGG GGG CTT TGT TAT GTG ATA CCT ACT ATT CCC AGC CCA TTT TGT
GAC TTA CCC CCC GAA ACA ATA CAC TAT GGA TGA TAA GGG TCG GGT AAA ACA 125                                             150
AGG TGC GTT GAA AAC TAT ACA GGA GCT CGT TGT GAA GAG GTT TTT CTC CCA
TCC ACG CAA CTT TTG ATA TGT CCT CGA GCA ACA CTT CTC CAA AAA GAG GGT 175                                             200
GGC TCC AGC ATC CAA ACT AAA AGT AAC CTG TTT GAA GCT TTT GTG GCA TTG
CCG AGG TCG TAG GTT TGA TTT TCA TTG GAC AAA CTT CGA AAA CAC CGT AAC 225                                             250
GCG GTC CTA GTA ACA CTT ATC ATT GGA GCC TTC TAC TTC CTT TGC AGG AAA
CGC CAG GAT CAT TGT GAA TAG TAA CCT CGG AAG ATG AAG GAA ACG TCC TTT 275                                             300
GGC CAC TTT CAG AGA GCC AGT TCA GTC CAG TAT GAT ATC AAC CTG GTA GAG
CCG GTG AAA GTC TCT CGG TCA AGT CAG GTC ATA CTA TAG TTG GAC CAT CTC

325
ACG AGC AGT ACC AGT GCC CAC CAC AGT CAT GAA CAA CAC TGA
TGC TCG TCA TGG TCA CGG GTG GTG TCA GTA CTT GTT GTG ACT
```

*Fig. 2*

Sequence Range: 1 to 348

```
                              25                                                  50
ATG CCA ACA GAT CAC GAG CAG CCC TGT GGT CCC AGG CAC AGG TCA TTT TGC
TAC GGT TGT CTA GTG CTC GTC GGG ACA CCA GGG TCC GTG TCC AGT AAA ACG 75                                                  100
CTC AAT GGG GGG ATT TGT TAT GTG ATC CCT ACT ATC CCC AGC CCA TTC TGT
GAG TTA CCC CCC TAA ACA ATA CAC TAG GGA TGA TAG GGG TCG GGT AAG ACA 125                                                 150
AGG TGC ATT GAA AAT TAC ACC GGA GCA CGC TGC GAA GAG GTT TTT CTC CCA
TCC ACG TAA CTT TTA ATG TGG CCT CGT GCG ACG CTT CTC CAA AAA GAG GGT 175                                                 200
AGC TCC AGC ATC CCA AGC GAA AGT AAT CTG TCG GCA GCT TTC GTG GTG CTG
TCG AGG TCG TAG GGT TCG CTT TCA TTA GAC AGC CGT CGA AAG CAC CAC GAC 225                                                 250
GCG GTC CTC CTC ACT CTT ACC ATC GCG GCG CTC TGC TTC CTG TGC AGG AAG
CGC CAG GAG GAG TGA GAA TGG TAG CGC CGC GAG ACG AAG GAC ACG TCC TTC 275                                                 300
GGC CAC CTT CAG AGG GCC AGT TCA GTC CAG TGT GAG ATC AGC CTG GTA GAG
CCG GTG GAA GTC TCC CGG TCA AGT CAG GTC ACA CTC TAG TCG GAC CAT CTC

325
ACA AAC AAT ACC AGA ACC CGT CAC AGC CAC AGA GAA CAC TGA
TGT TTG TTA TGG TCT TGG GCA GTG TCG GTG TCT CTT GTG ACT
```

*Fig. 3*

| Sample | Experiment 1 | Experiment 2 |
| --- | --- | --- |
| 2 (antisense) | 0/9 | 0/10 |
| 3 (sense) | 3/9 | 8/8 |
| 4 (sense) | 7/7 | 11/11 |

*Fig. 4*

EGFH2 GENES AND GENE PRODUCTS

CROSS REFERENCE TO RELATED APPLICATION(S)

This application is a Divisional of U.S. patent application Ser. No. 09/640,041 filed Aug. 15, 2000, issued Nov. 30, 2004, as U.S. Pat. No. 6,825,333, which claims the benefit of U.S. Provisional Application No. 60/149,986 filed Aug. 20, 1999.

TECHNICAL FIELD

The present invention relates to novel nucleic acid sequences encoding a member of the neuregulin family and to polypeptides encoded by the nucleic acid sequences.

BACKGROUND OF THE INVENTION

The ErbB/HER family of growth factor receptors plays an important role in cell signaling during development and proliferation. Several ErbB/HER family members are associated with human diseases, including, for example, cancer. Numerous ligands which bind and activate ErbB/HER receptors have been identified, including epidermal growth factor (EGF), epiregulin, amphiregulin and members of the neuregulin family (Ben-Baruch et al., *Hormones and growth factors in development and neoplasia*. Dickson R B and Salomon D S (eds). Kulwer Academic Publishers: Boston, pp. 145-168, 1988; Burden and Yarden, *Neuron* 18:847-855). Because signal transduction pathways involving ErbB/HER family members are associated with human disease, there is a need in the art for ligands which signal through these receptors. The ligand proteins and the genes encoding them are useful for therapeutic purposes.

This invention provides a gene of the neuregulin family and polypeptides encoded by the gene. The invention is directed to mRNA expressed by mammalian cells, polynucleotides having coding regions corresponding to the mRNAs, protein and polypeptide products of the polynucleotides and mRNAs, and biological functions of the polypeptides and proteins.

SUMMARY OF THE INVENTION

It is an object of the invention to provide EGFH2 polynucleotides and polypeptides.

One embodiment of the invention provides a composition comprising an isolated nucleic acid molecule comprising a polynucleotide selected from the group consisting of:
 (a) a polynucleotide encoding amino acids from about 1 to about 115 of SEQ ID NO:2;
 (b) a polynucleotide encoding amino acids from about 2 to about 115 of SEQ ID NO:2;
 (c) a polynucleotide encoding amino acids from about 1 to about 115 of SEQ ID NO:4;
 (d) a polynucleotide encoding amino acids from about 2 to about 115 of SEQ ID NO:4;
 (e) the polynucleotide complement of the polynucleotide of (a), (b), (c), or (d); and
 (f) a polynucleotide at least 90% identical to the polynucleotide of (a), (b), (c), (d) or (e).

Another embodiment of the invention provides a composition comprising an isolated nucleic acid molecule comprising about 345 contiguous nucleotides from the coding region of SEQ ID NO:1 or SEQ ID NO:3.

In another embodiment, the invention provides a composition comprising an isolated nucleic acid molecule comprising a polynucleotide encoding a polypeptide wherein, except for at least one conservative amino acid substitution, said polypeptide has an amino acid sequence selected from the group consisting of:
 (a) amino acids from about 1 to about 115 of SEQ ID NO:2;
 (b) amino acids from about 2 to about 115 of SEQ ID NO:2;
 (c) amino acids from about 1 to about 115 of SEQ ID NO:4;
 (d) amino acids from about 2 to about 115 of SEQ ID NO:4.

In a preferred embodiment of the invention, the isolated nucleic acid molecule is DNA.

Another embodiment of the invention provides a method of making a recombinant vector comprising inserting the nucleic acid molecule into a vector in operable linkage to a promoter. The invention further provides a recombinant vector produced by this method.

In another embodiment, the invention provides a method of making a recombinant host cell comprising introducing recombinant vector into a host cell. The invention further provides a host cell produced by this method.

A further object of the invention is to provide a recombinant method of producing a polypeptide comprising culturing the recombinant host cell under conditions such that said polypeptide is expressed and recovering said polypeptide.

The present invention provides an isolated polypeptide comprising amino acids at least 95% identical to amino acids selected from the group consisting of:
 (a) amino acids from about 1 to about 115 of SEQ ID NO:2;
 (b) amino acids from about 2 to about 115 of SEQ ID NO:2;
 (c) amino acids from about 1 to about 115 of SEQ ID NO:4; and
 (d) amino acids from about 2 to about 115 of SEQ ID NO:4.

A preferred embodiment of the invention provides an isolated polypeptide wherein, except for at least one conservative amino acid substitution, said polypeptide has an amino acid sequence selected from the group consisting of (a), (b), (c), or (d) above.

In a most preferred embodiment, the invention provides an isolated polypeptide comprising amino acids selected from the group consisting of (a), (b), (c), or (d) above.

In a most preferred embodiment, the polypeptides comprise a biologically active EGFH2 polypeptide. In a preferred embodiment, the polypeptides comprise a precursor or mature EGFH2 protein. In another preferred embodiment, the polypeptides comprise an EGFH2 EGF-like domain.

A further embodiment of the invention provides a polypeptide comprising an epitope-bearing portion of a polypeptide selected from SEQ ID NO:2 or SEQ ID NO:4.

A preferred embodiment provides an epitope-bearing portion of the polypeptide, which comprises between about 10 and 100 contiguous amino acids of SEQ ID NO:2 or SEQ ID NO:4.

A more preferred embodiment of the invention provides an epitope-bearing portion of the polypeptide which comprises between about 12 and 50 contiguous amino acids of SEQ ID NO:2 or SEQ ID NO:4.

A most preferred embodiment of the invention provides an epitope-bearing portion of the polypeptide which comprises between about 15 and 25 contiguous amino acids of SEQ ID NO:2 or SEQ ID NO:4.

The invention further provides a composition comprising an isolated antibody that binds specifically to polypeptides of the present invention.

In preferred embodiments, the antibodies are monoclonal, polyclonal or single-chain antibodies.

An object of the invention is to provide a method for detecting EGFH2 polypeptides or mRNA for diagnostic and prognostic purposes.

In a preferred embodiment, the method comprises an antibody which binds a polynucleotide of the invention, contacting the antibody with a biological sample from a human suspected of having a EGFH2 protein-modulated disorder under binding conditions to form a duplex, and determining the amount of said duplex formed, compared to a normal sample.

In another preferred embodiment, the method comprises a polynucleotide that binds to mRNA encoding a polypeptide of the invention under stringent conditions, contacting nucleic acid of said sample with said polynucleotide under binding conditions to form a duplex, and determining the amount of said duplex formed, compared to a normal sample.

In another preferred embodiment, the polynucleotide is a retroviral vector comprising a promoter and polynucleotides of the invention or complements thereof.

In yet another embodiment, patients are treated with a therapeutically effective amount of polypeptides capable of binding a polypeptide of the invention.

In a most preferred embodiment, the polypeptides are antibodies.

In another preferred embodmeier, the polypeptides are wild-type or mutant receptors for EGFH2.

In another embodiment of the invention, patients are treated with polypeptides of the invention.

BRIEF DESCRIPTION OF THE DRAWINGS

FIG. 1. Amino acid sequence alignment of human EGFH2 (SEQ ID NO:4) and mouse EGFH2 (SEQ ID NO:2). Stars indicate conserved residues.

FIG. 2. Human EGFH2 polynucleotide sequence (SEQ ID NO:3).

FIG. 3. Mouse EGFH2 polynucleotide sequence (SEQ ID NO:1).

FIG. 4. Effect of EGFH2 mRNA on *Xenopus oocyte* maturation.

DETAILED DESCRIPTION OF THE INVENTION

Neuregulins are a family of structurally related polypeptides, members of which regulate cellular proliferation, differentiation, apoptosis, and cell survival (reviewed in Carraway and Burden, *Curr. Opin. Neurobiol* 5:1-7 (1995)). In vivo studies demonstrated that disruption of neuregulin-1 is associated with cardiac and neural abnormalities, indicating that neuregulins play an important role in cardiac and neural development (Meyer and Birchmeier, *Nature* 378:386-390 (1995)). Furthermore, expression and signaling by certain neuregulin family members was altered following nerve injury and degeneration (Carroll et al., *J Neurosc.* 17:1642-1659 (1997)). Thus, neuregulins are important therapeutic targets for a number of indications, including, for example, cancers such as breast cancer, prostate cancer, oral cancer and ovarian cancer; heart diseases and injuries such as myocardial infarction and ischemia; wound healing such as bone fractures, tissue repair and regeneration; skin conditions such as burns, cuts, and ulcers; neurological conditions such as neuro-degenerative disease and stroke, multiple sclerosis, peripheral neuropathy, amyotrophic lateral sclerosis, dementia, Alzheimer's disease, Parkinson's disease, and Huntington's disease, brain injury, acute spinal cord injury, nervous system injury and peripheral nerve injury; infection, dementia, epilepsy, and acoustic trauma.

Neuregulins mediate cellular responses through interactions with their receptors, transmembrane tyrosine kinases of the ErbB family (reviewed in Burden and Yarden, *Neuron* 18:847-855 (1997)). These receptors function as homo- and heterodimers. Different receptor combinations exhibit different binding affinities for neuregulins and different abilities to activate downstream signaling complexes and promote cell proliferation. Neuregulin-1 (NRG1) and neuregulin-2 (NRG2) bind directly to the ErbB3 and ErbB4 receptor but can recruit ErbB1 and ErbB2 as coreceptors. Targeted disruption in mice of the genes encoding ErbB2 and ErbB4 result in heart malformations and defects in the nervous system (Lee et al., *Nature* 378:386-390 (1995); Gassmann et al., *Nature* 378:390-394 (1995)). However, the specific neural defects differ between ErbB2 and ErbB4 homozygous mutant mice (discussed in Carraway, *BioEssays* 18:263-266 (1996). These findings demonstrate that specific receptors play different roles in cell growth and development. Since different receptor dimers preferentially bind specific ligands, there is a need for the identification of novel ligands of the neuregulin family.

The neuregulins constitute a subfamily of the epidermal growth factor (EGF) family. Neuregulins contain a characteristic receptor-binding EGF-like motif with six conserved cysteine residues. Neuregulins may contain other extracellular motifs, including a signal peptide, a cysteine-containing N-terminal domain, either a cysteine-rich domain (CRD) or a domain distantly related to a kringle motif, an Ig-like loop, a glycosylation domain, and a transmembrane domain (Burden and Yarden, *Neuron* 18:847-855 (1997)). Depending on the presence or absence of the transmembrane domain, neuregulin precursors may be either transmembrane proteins or secreted polypeptides. The most highly conserved region of neuregulins is their EGF-like domain.

Three members of the neuregulin family were identified, including NRG1, NRG2, and NRG3. Multiple isoforms of NRG1 and NRG2 exist, some of which display heterogeneous binding affinities for different ErbB receptors (Tzahar et al., *J. Biol. Chem.* 269:25226-25233 (1994); Pinkas-Kramarski et al., *Mol. Cell. Biol.* 18:6090-6101 (1998)). The different NRG1 isoforms result from alternative splicing of a single gene (Carraway, *BioEssays* 18:263-266 (1996)). The present invention discloses polypeptides and polynucleotides encoding a novel member of the neuregulin family of proteins, termed EGFH2. EGFH2 is expressed in specific tissues during development and promotes meiotic maturation of *Xenopus oocytes*. In humans, EGFH2 is expressed in skeletal muscle and pancreas cells, and EGFH2 levels are elevated in pancreatic tumor tissue as compared to normal pancreatic samples.

EGFH2 Nucleic Acids, Polypeptides and Antibodies.

The invention provides a full length mouse cDNA encoding a predicted 115 amino acid protein with homology to proteins of the neuregulin subfamily of the EGF proteins, referred to as mEGFH2. The nucleotide sequence of mEGFH2 is shown in SEQ ID NO:1. The predicted polypeptide sequence encoded by mEGFH2 is shown in SEQ ID NO:2.

The invention also provides a human homolog of the mouse EGFH2 gene. The predicted open reading frame of the human EGFH2 clone (hEGFH2) encodes a 115 amino acid protein. The nucleotide sequence of hEGFH2 is shown in SEQ ID NO:3. The amino acid sequence of the polypeptide encoded by hEGFH2 is shown in SEQ ID NO:4. The mEGFH2 and hEGFH2 protein sequences are 76% identical (FIG. 1). Percent identity between these sequences refers to identity as calculated using the Smith-Waterman homology search algorithm as implemented in MPSRCH program (Oxford Biomolecular) using an affine gap search with the following search parameters: gap open penalty, 12; gap extension penalty, 1.

PCR amplification using oligonucleotides which hybridize to SEQ ID NO:1 or SEQ ID NO:3 can also be used to obtain mouse or human EGFH2 polynucleotides, using either genomic DNA or cDNA as a template. Polynucleotide molecules of the invention can also be made using the techniques of synthetic chemistry given the sequences disclosed herein. The degeneracy of the genetic code permits alternate nucleotide sequences which will encode the amino acid sequences presented in SEQ ID NO:2 and SEQ ID NO:4 to be synthesized. All such nucleotide sequences are within the scope of the present invention.

The present invention includes nucleic acid sequences that encode mouse or human EGFH2. Also included within the scope of the invention are sequences that are substantially the same as the nucleic acid sequences encoding EGFH2. Such substantially same sequences may, for example, be substituted with codons more readily expressed in a given host cell such as E. coli according to well known and standard procedures. The present invention also includes nucleic acid sequences which will hybridize to sequences which encode human or mouse EGFH2 or complements thereof. Such nucleic acid sequences can be at least 90%, 91%, 92%, 93% or 94% identical, preferably 95%, 96%, 97%, 98% or 99% identical. The invention includes nucleic acid sequences encoding functional domains of EGFH2, such as, for example, the EGF-like domain. In addition, the invention includes nucleic acids that encode polypeptides that are recognized by antibodies that bind either mEGFH2 or hEGFH2 polypeptides.

Isolated genes corresponding to the cDNA sequences disclosed herein are also provided. Known methods can be used to isolate the corresponding genes using the provided cDNA sequences. These methods include preparation of probes or primers from the nucleotide sequences shown in SEQ ID NO:1 and SEQ ID NO:3 for use in identifying or amplifying the genes from genomic libraries or other sources of genomic DNA. Polypeptides encoded by the isolated genes are within the scope of the invention. These polypeptides include, but are not limited to, polypeptides encoded by the cDNAs comprising SEQ ID NO:1 and SEQ ID NO:3 and isoforms of these polypeptides resulting from alternative splicing of the isolated genes.

The present invention encompasses vectors comprising expression regulatory elements operably linked to any of the nucleic acid sequences included within the scope of the invention. Vectors may include, but are not limited to, plasmids, episomes, retroviruses, lentivirus, adenovirus, and parvoviruses including adeno-associated virus. This invention also includes host cells, of any variety, that have been transformed with vectors comprising expression regulatory elements operably linked to any of the nucleic acid sequences included within the scope of the present invention. Examples of host cells include bacterial cells, yeast, plants, tissue culture cells including primary, immortalized and transformed cell lines, and insect cells.

Examination of EGFH2 mRNA expression by northern blot analysis revealed that EGFH2 is expressed in a limited number of tissues in both mouse and human. Numerous mRNA species were detected (see Example 2), indicating that multiple EGFH2 polypeptides may be expressed. These polypeptides can result from differential splicing of a single EGFH2 gene or the existence of more than one closely related EGFH2 gene. All EGFH2 isoforms resulting from differential splicing of a single EGFH2 gene and all related EGFH2 genes are within the scope of this invention.

The present invention also includes polypeptide sequences including sequences corresponding to mouse and human EGFH2.

Reference to EGFH2 herein is intended to include growth factors of any origin which are substantially homologous to and which are biologically equivalent to the EGFH2 characterized and described herein. Such substantially homologous growth factors may be native to any tissue or species and, similarly, biological activity can be characterized in any of a number of biological assay systems. For example, biological activity can be determined using an assay to measure the effect of a given polynucleotide or corresponding mRNA on germinal vesicle breakdown in *Xenopus oocytes* as described in Example 3.

The term "biologically equivalent" is intended to mean that the compositions of the present invention are capable of demonstrating some or all of the same growth properties in a similar fashion, not necessarily to the same degree as the EGFH2 as described herein or recombinantly produced EGFH2 of the invention.

Sequence identity or percent identity is intended to mean the percentage of same residues between two sequences, when the two sequences are aligned using, for example, the Clustal method (Higgins et al., *Cabios* 8:189-191 (1992)) of multiple sequence alignment in the Lasergene biocomputing software (DNASTAR, Inc., Madison, Wis.). In this method, multiple alignments are carried out in a progressive manner, in which larger and larger alignment groups are assembled using similarity scores calculated from a series of pairwise alignments. Optimal sequence alignments are obtained by finding the maximum alignment score, which is the average of all scores between the separate residues in the alignment, determined from a residue weight table representing the probability of a given amino acid change occurring in two related proteins over a given evolutionary interval. Penalties for opening and lengthening gaps in the alignment contribute to the score. The default parameters used with this program are as follows: gap penalty for multiple alignment=10; gap length penalty for multiple alignment=10; k-tuple value in pairwise alignment=1; gap penalty in pairwise alignment=3; window value in pairwise alignment=5; diagonals saved in pairwise alignment=5. The residue weight table used for the alignment program is PAM250 (Dayhoff et al., in *Atlas of Protein Sequence and Structure*, Dayhoff, Ed., NDRF, Washington, Vol. 5, suppl. 3, p. 345, 1978).

Percent conservation is calculated from the above alignment by adding the percentage of identical residues to the percentage of positions at which the two residues represent a conservative substitution (defined as having a log odds value of greater than or equal to 0.3 in the PAM250 residue weight table). Conservative amino acid changes satisfying this requirement are: R-K; E-D, Y-F, L-M; V-I, Q-H.

The invention provides EGFH2 proteins or variants thereof having one or more polymers covalently attached to one or more reactive amino acid side chains. By way of example, not limitation, such polymers include polyethylene glycol (PEG), which can be attached to one or more free cysteine sulfhydryl residues, thereby blocking the formation of disulfide bonds and aggregation when the protein is exposed to oxidizing conditions. In addition, pegylation of EGFH2 proteins and/or muteins is expected to provide such improved properties as increased half-life, solubility, and protease resistance. EGFH2 proteins and/or muteins may alternatively be modified by the covalent addition of polymers to free amino groups such as the lysine epsilon or the N-terminal amino group.

Preferred cysteines and lysines for covalent modification will be those not involved in receptor binding. It will be apparent to one skilled in the art that the methods for assaying EGFH2 biochemical and/or biological activity may be employed in order to determine if modification of a particular amino acid residue affects the activity of the protein as desired.

It may be advantageous to improve the stability of EGFH2 by modifying one or more protease cleavage sites. Thus, the present invention provides EGFH2 variants in which one or more protease cleavage site has been altered by, for example, substitution of one or more amino acids at the cleavage site in order to create an EGFH2 variant with improved stability. Such improved protein stability may be beneficial during protein production and/or therapeutic use. Suitable protease cleavage sites for modification are well known in the art and likely will vary depending on the particular application contemplated.

Fusion proteins comprising EGFH2 or a biologically active or antigenic fragment thereof can be produced using methods known in the art. Such fusion proteins can be used therapeutically or can be produced in order to simplify the isolation and purification procedures. Histidine residues can be incorporated to allow immobilized metal affinity chromatography purification. Residues EQKLISEEDL contain the antigenic determinant recognized by the myc monoclonal antibody and can be incorporated to allow myc monoclonal antibody-based affinity purification. A thrombin cleavage site can be incorporated to allow cleavage of the molecule at a chosen site; a preferred thrombin cleavage site is residues LVPRG. Purification of the molecule can be facilitated by incorporating a sequence, such as residues SAWRHPQFGG, which binds to paramagnetic streptavidin beads. Such embodiments are described in WO 97/25345, which is incorporated by reference.

EGFH2 can also include hybrid and modified forms of EGFH2 including fusion proteins and EGFH2 fragments and hybrid and modified forms in which certain amino acids have been deleted or replaced and modifications such as where one or more amino acids have been changed to a modified amino acid or unusual amino acid and modifications such as glycosylations so long as the hybrid or modified form retains the biological activity of EGFH2. Polypeptides comprising conserved structural or functional domains of EGFH2, such as, for example, the EGF-like domain, are included within the scope of the invention. The EGF-like domain of neuregulins can bind specific ErbB/HER receptors (reviewed in Burden and Yarden, *Neuron* 18:847-855 (1997)). Other regions of neuregulins may play a role in recruiting receptor dimerization partners. An isolated EGFH2 EGF-like domain can affect receptor dimer formation and function. For example, an isolated EGFH2 EGF-like domain can direct formation of specific receptor dimers which may be different from those induced by full length EGFH2, or an isolated EGFH2 EGF-like domain may prevent receptor dimerization by failing to recruit a coreceptor. Similarly, amino acid substitutions in a region of EGFH2 involved in coreceptor recruitment may affect dimer formation. The ability of EGFH2 and mutants to affect receptor dimer formation can be examined by incubating cells expressing various ErbB/HER receptors with purified EGFH2 or epitope-tagged EGFH2. Antibodies directed against EGFH2 or the epitope tag are used to immunoprecipitate EGFH2 and associated receptors according to procedures well established in the art. Coprecipitating receptors can be identified by western blot analysis using antibodies specific for different receptors or by performing the immunoprecipitations using radiolabeled cells. Isolated EGFH2 EGF-like domains and EGFH2 mutants that affect receptor dimer formation are within the scope of the present invention.

The invention also includes fragments of EGFH2. Preferred fragments include: amino acids from about 9 to about 45; amino-acids from about 4 to about 50; amino acids from about 4 to about 82; amino acids from about 1 or 2 to 50; and amino acids from about 1 or 2 to about 82. Such fragments can be prepared from the protein by standard biochemical methods or by expressing a polynucleotide encoding the fragment.

Also included with the scope of the invention are EGFH2 molecules that differ from native EGFH2 by virtue of changes in biologically active sites. EGFH2 has a putative transmembrane domain at amino acid residues 63-82. An EGFH2 molecule that does not include this transmembrane domain can be prepared by expressing DNA encoding EFGH2, wherein the corresponding codons for some or all of amino acid residues 63-82 have been deleted. DNA encoding EGFH2 with altered receptor binding can likewise be produced. The EGF-like receptor binding domain of EGFH2 extends from approximately amino acid 4 to amino acid 50. For example, it may be desirable to alter receptor specificity of EGFH2 by substituting the receptor binding regions of a different neuregulin or other EGF-like domain for that of EGFH2.

Also included within the meaning of substantially homologous is any EGFH2 which may be isolated by virtue of cross-reactivity with antibodies to the EGFH2 described herein or whose encoding nucleotide sequences including genomic DNA, mRNA or cDNA may be isolated through hybridization with the complementary sequence of genomic or subgenomic nucleotide sequences or cDNA of the EGFH2 herein or fragments thereof. It will also be appreciated by one skilled in the art that degenerate DNA sequences can encode human or mouse EGFH2 and these are also intended to be included within the present invention as are allelic variants of EGFH2.

Recombinant human or mouse EGFH2 may be made by expressing the DNA sequences encoding EGFH2 in a suitable transformed host cell. Using methods well known in the art, the DNA encoding EGFH2 may be linked to an expression vector, transformed into a host cell and conditions established that are suitable for expression of EGFH2 by the transformed cell.

The DNA encoding EGFH2 can be engineered to take advantage of preferred codon usage of host cells. Codon usage in *Pseudomonas aeruginosa* is described in, for example, West et al., *Nucleic Acids Res.* 11:9323-9335 (1988). Codon usage in *Saccharomyces cerevisiae* is described in, for example, Lloyd et al., *Nucleic Acids Res.* 20:5289-5295 (1992). Codon preference in *Corynebacteria* and a comparison with *E. coli* preference is provided in Malubres et al., *Gene* 134:15-24 (1993). Codon usage in *Drosophila melanogaster* is described in, for example, Akashi, *Genetics* 136:927-935 (1994).

Any suitable expression vector may be employed to produce recombinant human or mouse EGFH2 such as expression vectors for use in insect cells. Baculovirus expression systems can also be employed. A preferable method is expression in insect cells, such as Tr5 or Sf9 cells, using baculovirus vector.

The present invention includes nucleic acid sequences including sequences that encode human or mouse EGFH2. Also included within the scope of this invention are sequences that are substantially the same as the nucleic acid sequences encoding EGFH2. Such substantially the same sequences may, for example, be substituted with codons more readily expressed in a given host cell such as *E. coli* according to well known and standard procedures. Such modified nucleic acid sequences are included within the scope of this invention.

Specific nucleic acid sequences can be modified by those skilled in the art and, thus, all nucleic acid sequences that code for the amino acid sequences of EGFH2 can likewise be so modified. The present invention thus also includes nucleic acid sequence which will hybridize with all such nucleic acid sequences—or complements of the nucleic acid sequences where appropriate—and encode a polypeptide having the biologically equivalent activities of EGFH2 such as those disclosed herein. The present invention also includes nucleic acid sequences that encode polypeptides that have the biologically equivalent activities of EGFH2 and that are recognized by antibodies that bind to EGFH2.

The present invention also encompasses vectors comprising expression regulatory elements operably linked to any of the nucleic acid sequences included within the scope of the invention. This invention also includes host cells of any variety that have been transformed with vectors comprising expression regulatory elements operably linked to any of the nucleic acid sequences included within the scope of the present invention.

Methods are also provided herein for producing EGFH2. Preparation can be by isolation from conditioned medium from a variety of cell types so long as the cell type produces EGFH2. A second and preferred method involves utilization of recombinant methods by isolating or obtaining a nucleic acid sequence encoding EGFH2, cloning the sequence along with appropriate regulatory sequences into suitable vectors and cell types, and expressing the sequence to produce EGFH2.

EGFH2 polypeptides containing one or more amino acid substitutions are included within the invention. Amino acid changes in variants or derivatives of proteins of the invention may be conservative substitutions. A conservative amino acid change involves substitution of one amino acid for another amino acid of a family of amino acids with structurally related side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, arparagine, glutamine, cysteine, serine, threonine, tyrosine) amino acids. Phenylalanine, tryptophan, and tyrosine are sometimes classified as aromatic amino acids. Non-naturally occurring amino acids can also be used to form protein variants of the invention.

Whether an amino acid change results in a functional protein or polypeptide can be readily determined by assaying biological properties of the disclosed proteins or polypeptides. For example, mitogenic biological properties can be measured by examining the effect of the protein or polypeptide's expression on *Xenopus oocyte* maturation, as discussed in Example 3.

Standard biochemical methods can be used to isolate proteins of the invention from tissues which express the proteins or to isolate proteins, polypeptides, or fusion proteins from recombinant host cells into which a DNA construct has been introduced. Methods of protein purification, such as size exclusion chromatography, ammonium sulfate crystallization, electrofocusing, or preparative gel electrophoresis, are well known and widely used in the art. Synthetic chemistry methods, such as solid phase peptide synthesis, can be used to synthesize proteins, fusion proteins, or polypeptides of the invention.

Recombinant EGFH2 may be made by expressing the DNA sequences encoding mouse or human EGFH2 in a suitable transformed host cell. Using methods well known in the art, the DNA encoding EGFH2 may be linked to an expression vector, transformed into a host cell and conditions established that are suitable for expression of EGFH2 by the transformed cell. Any suitable expression vector may be employed to produce recombinant human or mouse EGFH2 such as expression vectors for use in bacterial cells, yeast cells or insect cells. Baculovirus expression systems can also be employed. One preferred method is expression in insect cells, such as Tr5 or Sf9 cells, using baculovirus vector. Another method to produce EGFH2 is to isolate EGFH2 from conditioned medium from a variety of cell types so long as the cell type produces EGFH2. Such cells may include, but are not limited to, primary cells, immortalized cells, transformed cells, or cells transiently or stably transfected or infected with a vector or virus expressing EGFH2.

The resulting expressed protein can be purified from the culture medium or from extracts of the cultured cells using purification procedures known in the art. For example, for proteins fully secreted into the culture medium, cell-free medium can be diluted with sodium acetate and contacted with a cation exchange resin, followed by hydrophobic interaction chromatography. Using this method, the desired polypeptide is typically greater than 95% pure. Further purification can be undertaken, using, for example, any of the techniques listed above. Proteins, fusion proteins, or polypeptides can also be tagged with an epitope, such as a "Flag" epitope (Kodak), and purified using an antibody which specifically binds to the epitope.

It may be necessary to modify a protein produced in yeast or bacteria, for example, by phosphorylation or glycosylation of the appropriate sites, in order to obtain a functional protein. Such covalent modifications can be made using known chemical or enzymatic methods.

Proteins or polypeptides of the invention can also be expressed in cultured cells in a form which will facilitate purification. For example, a secreted protein or polypeptide can be expressed as a fusion protein comprising, for example, maltose binding protein, glutathione-S-transferase, or thioredoxin, and purified using a commercially available kit. Kits for expression and purification of such fusion proteins are available from companies such as New England BioLabs, Pharmacia, and Invitrogen.

The present invention provides both full-length and mature forms of the disclosed proteins. Full length forms of the proteins have amino acid sequences shown in SEQ ID NO:2 and SEQ ID NO:4. The full length forms of a protein can be processed enzymatically to remove a signal sequence, resulting in a mature form of a protein. Signal sequences can be identified by examination of the amino acid sequences disclosed herein and comparison with amino acid sequences of known signal sequences (see, e.g., von Heigne, (1985) "Signal Sequences: The Limits of Variation" *J. Mol. Biol.* 184: 99-105 and Kaiser and Botstein, (1986) *Mol. Cell. Biol.* 6:2382.)

Polypeptides consisting of less than full length proteins of the present invention are also provided. Polypeptides of the invention can be linear or cyclized. Polypeptides can be used, for example, as immunogens, diagnostic aids, or therapeutics. Polypeptides of less than the entire amino acid sequence shown in SEQ ID NO:2 and SEQ ID NO:4 are similarly provided.

Polypeptide Fragments

The invention provides polypeptide fragments of the disclosed protein. Polypeptide fragments of the invention can comprise at least 8, 10, 12, 15, 18, 19, 20, 25, 50, 75, 100, 105, 110, or 112 contiguous amino acids selected from SEQ ID NO:2 or 4. Also included are all intermediate length fragments in this range, such as 21, 22, 23, etc.; 51, 52, 53, etc.; and 76, 77, 78, etc., which are exemplary only and not limiting.

Biologically Active Variants

Variants of the protein and polypeptides disclosed herein can also occur. Variants can be naturally or non-naturally occurring. Naturally occurring variants are found in humans or other species and comprise amino acid sequences which are substantially identical to the amino acid sequence shown in SEQ ID NO:2 or 4. Species homologs of the protein can be obtained using subgenomic polynucleotides of the invention, as described below, to make suitable probes or primers to screening cDNA expression libraries from other species, such as mice, monkeys, yeast, or bacteria, identifying cDNAs which encode homologs of the protein, and expressing the cDNAs as is known in the art.

Non-naturally occurring variants which retain substantially the same biological activities as naturally occurring protein variants are also included here. Preferably, naturally or non-naturally occurring variants have amino acid sequences which are at least 85%, 90%, or 95% identical to the amino acid sequence shown in SEQ ID NO:2 or 4. More preferably, the molecules are at least 98% or 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* (1981) 2:482-489.

Guidance in determining which amino acid residues can be substituted, inserted, or deleted without abolishing biological or immunological activity can be found using computer programs well known in the art, such as DNASTAR software. Preferably, amino acid changes in secreted protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting variant.

Variants of the EGFH2 protein disclosed herein include glycosylated forms, aggregative conjugates with other molecules, and covalent conjugates with unrelated chemical moieties. Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

A subset of mutants, called muteins, is a group of polypeptides in which neutral amino acids, such as serines, are substituted for cysteine residues which do not participate in disulfide bonds. These mutants may be stable over a broader temperature range than native secreted proteins. See Mark et al., U.S. Pat. No. 4,959,314.

Preferably, amino acid changes in the EGFH2 protein or polypeptide variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting secreted protein or polypeptide variant. Properties and functions of EGFH2 protein or polypeptide variants are of the same type as a protein comprising the amino acid sequence encoded by the nucleotide sequence shown in SEQ ID NO:1 or 3, although the properties and functions of variants can differ in degree.

EGFH2 protein variants include glycosylated forms, aggregative conjugates with other molecules, and covalent conjugates with unrelated chemical moieties. EGFH2 protein variants also include allelic variants, species variants, and muteins. Truncations or deletions of regions which do not affect the differential expression of the EGFH2 protein gene are also variants. Covalent variants can be prepared by linking functionalities to groups which are found in the amino acid chain or at the N- or C-terminal residue, as is known in the art.

It will be recognized in the art that some amino acid sequence of the EGFH2 protein of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the polypeptides of the present invention may include one or more amino acid substitutions, deletions or additions, either from natural mutations or human manipulation.

The invention further includes variations of the EGFH2 polypeptide which show comparable expression patterns or which include antigenic regions. Such mutants include deletions, insertions, inversions, repeats, and type substitutions. Guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Of particular interest are substitutions of charged amino acids with another charged amino acid and with neutral or negatively charged amino acids. The latter results in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331-340 (1967); Robbins et al., *Diabetes* 36:838-845 (1987); Cleland et al., *Crit. Rev. Therapeutic Drug Carrier Systems* 10:307-377 (1993)).

Amino acids in the polypeptides of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

Antibodies to EGFH2 are provided by the invention. Antibodies of the invention can be used, for example, to detect polypeptides of the invention in culture medium or tissue samples. Antibodies may be polyclonal, monoclonal or single chain antibodies. Antibodies to mouse and human EGFH2 protein or an epitope thereof can be made by any of a number of methods known in the art. Detailed methods for generating antibodies are provided in Harlow and Lane, Antibodies: A Laboratory Manual, Cold Spring Harbor Laboratories, 1988, which is incorporated by reference. Methods of generating the antibodies are also described in U.S. patent application Ser. No. 08/988,671, which is incorporated by reference in its entirety. By epitope, reference is made to an antigenic determinant of a polypeptide. An epitope could comprise 3 amino acids in a spatial conformation which is unique to the epitope. Methods of determining the spatial conformation of amino acids are known in the art, and include, for example, x-ray crystallography and 2 dimensional nuclear magnetic resonance. Antibodies to EGFH2 can also be raised against oligopeptides that include one or more conserved regions identified herein such that the antibody can cross-react with other species and/or family members.

Polyclonal antibodies can be prepared by immunizing rabbits or other animals by injecting antigen followed by subsequent boosts at appropriate intervals. Animal sera is assayed for immunoreactivity against EGFH2 by any of a number of methods, including, for example, western blot or ELISA. Monoclonal antibodies can be prepared after the method of Milstein and Kohler by fusing splenocytes from immunized mice with continuously replicating tumor cells (Milstein and Kohler, *Nature* 256:495-497, 1975).

Techniques for purifying antibodies are those available in the art. In a preferred embodiment, antibodies are affinity purified by passing the antibodies over a column to which amino acid sequences of the invention are bound. Bound antibody is then eluted. Any technique may be chosen to purify antibodies of the invention.

Polypeptides encoded by EGFH2 can be used to screen peptide libraries to identify binding partners from among the encoded polypeptides. Candidate binding partners for EGFH2 include cell surface receptors and proteins which bind EGFH2 protein to form multimeric protein complexes. Such binding partners can be useful in treating cancer, hyperproliferation and related conditions. For example, peptides and antibodies capable of binding to an EGFH2 binding partner or receptor can block EGFH2 binding to said partner or receptor and thereby inhibit the biological activity of EGFH2. Polypeptide binding partners can be identified by any method available in the art such as expression cloning using a labeled EGFH2 polypeptide probe or yeast two-hybrid screening using a fusion protein comprising an EGFH2 polypeptide as bait. Yeast two-hybrid screens, also called interaction trap assays, are described, for example, in Gyuris et al., *Cell* 74:791-803 (1993). Binding partners can also be identified by low stringency immunoprecipitation using an antibody directed against an EGFH2 polypeptide followed by sequencing of coprecipitating polypeptides.

Peptide agonists and antagonists are screened using any available method, such as signal transduction, antibody binding, receptor binding, mitogenic assays, chemotaxis assays, etc. A library of peptides may be synthesized following the methods disclosed in U.S. Pat. No. 5,010,175 and in PCT WO91/1723. The assay conditions ideally should resemble the conditions under which the native activity is exhibited in vivo, that is, under physiologic pH, temperature, and ionic strength. Suitable agonists or antagonists will exhibit strong inhibition or enhancement of the native activity at concentrations that do not cause toxic side effects in the subject.

The end results of such screening and experimentation will be at least one novel EGFH2 protein binding partner, such as a receptor and at least one peptide agonist or antagonist of EGFH2. Such agonists and antagonists can be used to modulate, enhance, or inhibit EGFH2 protein function in cells.

Therapeutic and Diagnostic Uses of EGFH2.

Members of the neuregulin family influence cellular proliferation, differentiation, and apoptosis. For example, neuregulin-1 stimulates mitogenesis of mouse fibroblasts, human Schwann cells, epithelial and glial cells (Carraway et al., *J. Biol. Chem.* 270:7111-7116 (1995); Morrissey et al., *Proc. Natl. Acad. Sci. USA* 92:1431-1435 (1995); Peles and Yarden, *Bioessays* 15:815-824 (1993)). Neuregulin-1 also acts as a survival factor for astrocytes (Pinkas-Kramarski et al., *Proc. Natl. Acad. Sci. USA* 91:9387-9391 (1994)). Thus, neuregulins regulate cell growth and tissue homeostasis and represent important targets for treatment of diseases associated with aberrant cell growth, such as cancer, tumor progression, hyperproliferative cell growth or accompanying biological or physical manifestations. EGFH2 is a neuregulin family member which regulates cell proliferation. For example, EGFH2 induces meiotic maturation of *Xenopus oocytes*, as illustrated in FIG. 4.

Neuregulins are expressed in tissue- and stage-specific patterns. Neuregulin-1 isoforms are primarily expressed in neural and muscle tissue (discussed in Carraway, *Bioessays* 18:263-266 (1996)). Northern blot analysis of EGFH2 mRNA expression in various human tissues revealed that EGFH2 is primarily expressed in pancreas and skeletal muscle tissues (see Example 2). In situ hybridization of samples from human pancreas detected elevated levels of EGFH2 expression in a sample of human pancreatic tumor (see Example 2). Thus, according to the invention, EGFH2 is likely to play a role in pancreatic cancers. Analysis of murine EGFH2 expression in mouse embryos revealed that it is widely expressed throughout the embryo except in neural tube and limb areas. Thus, EGFH2 is likely to play a widespread role in promoting cell proliferation during development. Differences in the mRNA expression patterns of neuregulin-1 and EGFH2 demonstrate that their corresponding polypeptide products have distinct roles in cell growth and development. Therefore, inactivation of EGFH2 activity is likely to have important biological effects. Given the sequence homology between the neuregulin family members, it is likely that the family members share common biological properties. Thus, it is likely that EGFH2 can promote proliferation of cells other than those in which it is normally expressed or contacts. It is, therefore, within the scope of the invention to use EGFH2 polynucleotides and polypeptides to treat diseases or conditions which are not normally associated with EGFH2.

EGFH2 may be useful in the treatment of disorders of hearing, smell or taste due to loss/dysfunction of cells responsive to the molecule, including cranial or peripheral nerves, sensory cells, supporting cells, etc., and in treatment of peripheral motor or sensory nerve disease characterized by loss of function or death of neurons, nerves, other CNS or PNS cells or supporting cells: Amyotrophic Lateral Sclerosis, motor or sensory neuropathies (due to many causes: viral infections, metabolic disease, diabetes, autoimmune insult, idiopathic, degenerative) and trauma.

Cardiomyopathies characterized by loss of function or death of cardiac myocytes or supporting cells in the heart (congestive heart failure, myocarditis) may also be treated with EGFH2, as can arrhythmias, ischemic heart disease and correction of congenital defects. Musculoskeletal disease characterized by loss of function, inadequate function or death of skeletal muscle cells, bone cells or supporting cells may also be treated with EGFH2. Examples include inherited and acquired skeletal myopathies, bone disease, and arthritis. Other skeletal muscle conditions amenable to treatment include wasting due to systemic illness such as cancer, AIDS, heart failure, advanced age, and inactivity; and rhabdomyosarcomas. The EGFH2 of the invention may be a target for inhibitors or other modulators, or may be used as a differentiation factor to treat the condition directly. In patients with diabetes, EGFH2 of the invention may be useful in enhancing glucose utilization in skeletal muscle.

Ischemic vascular disease may be amenable to EGFH2 treatment. EGFH2 polynucleotides and polypeptides may aid in correction of congenital defects due to loss of a neuregulin or its function (heart, lung, brain, kidney, limbs, pancreas, etc.).

Pancreatic conditions that can be treated include disorders of the exocrine pancreas, particularly malabsorption related to exocrine failure; disorders of the endocrine pancreas, particularly diabetes; and pancreatitis and its related complications. Pancreatic cancer may be treated using inhibitors or other modulators of EGFH2. Alternatively or in addition, EGFH2 may be used as a differentiation factor to treat the cancer directly.

Treatment of wound healing is yet another use of EGFH2 polypeptides and polynucleotides. Examples include liver regeneration, operative wound healing, healing of traumatic wounds, healing of ulcers, bone fractures, metabolic disease, and loss of cells due to inflammatory disease.

The present invention includes methods of treating patients in need thereof with polynucleotides and polypeptides of the invention. Diseases and disorders which can be treated using compositions of the present invention include, but are not limited to, cancers including breast cancer, prostate cancer, pancreatic cancer, oral cancer, and ovarian cancer, peripheral neuropathy, amyotrophic lateral sclerosis, Alzheimer's disease, Parkinson's disease, Huntington's disease, ischemic stroke, brain injury, acute spinal cord injury, nervous system injury, multiple sclerosis, infection, dementia, epilepsy, peripheral nerve injury, acoustic trauma and tissue wound.

The present invention includes therapeutic or pharmaceutical compositions comprising the polynucleotides and polypeptides of the invention. Pharmaceutical compositions can comprise polypeptides, antibodies, small molecules or polynucleotides. Therapeutics, whether polynucleotide or polypeptide or small molecule, can be tested, for example, in animal models and cell lines disclosed in Bosland, *Encyclopedia of Cancer*, volume II, pages 1283 to 1296 and 1303 to 1313 (1997) by Academic Press. Pharmaceutical compositions may be designed to either decrease or increase EGFH2 activity, depending on the type of disease or disorder being treated. For example, cancers or diseases associated with hyperproliferation may be treated by reducing EGFH2 activity, for example, by administering therapeutically effective amounts of antisense EGFH2 RNA, EGFH2 ribozymes, inactivating antibodies, peptide or small molecule antagonists or inhibitors, EGFH2 mutants or EGFH2 receptors or mutants thereof. However, conditions or diseases that can be treated by promoting cell proliferation may be treated, for example, by administering biologically active EGFH2 polypeptides or an expression vector comprising EGFH2 polynucleotides encoding biologically active EGFH2 polypeptides.

The term "therapeutically effective amount" as used herein refers to an amount of a therapeutic agent to treat, ameliorate, or prevent a specific disease or condition, or to exhibit a detectable therapeutic or preventive effect. The effect can be detected by, for example, chemical markers or antigen levels. The effects also include reduction in physical symptoms. The effective amount for a given situation can be determined by routine experimentation and is within the judgment of the clinician. The precise effective amount will vary depending on factors including, but not limited to, the subject's size and health, the nature and extent of the condition, and the therapeutics selected for administration. For purposes of the present invention, an effective dose will be from about 0.01 mg/kg to 50 mg/kg or 0.05 mg/kg to about 10 mg/kg of the polynucleotide, polypeptide or antibody compositions in the individual to which it is administered.

A pharmaceutical composition can also contain a pharmaceutically acceptable carrier. The term "pharmaceutically acceptable carrier" refers to a carrier for administration of a therapeutic agent, such as antibodies, polypeptides, polynucleotides and other therapeutic agents. Suitable carriers and pharmaceutically acceptable salts are well known to those of ordinary skill in the art. A thorough discussion of pharmaceutically acceptable excipients is available in *Remington's Pharmaceutical Sciences* (Mack Pub. Co., N.J. 1991).

Once formulated, the polynucleotide and polypeptide compositions of the invention can be (1) administered directly to the subject; (2) delivered ex vivo, to cells derived from the subject; or (3) delivered in vitro for expression of recombinant proteins. Direct delivery of the compositions will generally be accomplished by injection, either subcutaneously, intraperitoneally, intravenously or intramuscularly, or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Methods for the ex vivo delivery and reimplantation of transformed cells into a subject are known in the art and described in e.g., International Publication No. WO 93/14778. Generally, delivery of nucleic acids for both ex vivo and in vitro applications can be accomplished by, for example, dextran-mediated transfection, calcium phosphate precipitation transfection, viral infection, polybrene mediated transfection, protoplast fusion, electroporation, encapsulation of the polynucleotide(s) in liposomes, and direct microinjection of the DNA into nuclei, all well known in the art.

Examples of polynucleotide therapeutic agents include ribozymes, antisense RNA, and mammalian expression vectors. Trans-cleaving catalytic RNAs (ribozymes) are RNA molecules possessing endoribonuclease activity. Ribozymes are engineered to cleave any RNA species site-specifically in the background of cellular RNA. The cleavage event renders the mRNA unstable and prevents protein expression. Ribozyme design and therapeutic uses are disclosed in Usman et al., *Current Opin. Struct. Biol.* (1996) 6:527-533, which is incorporated by reference. The EGFH2 polynucleotide sequence provides adequate sequence for constructing an effective ribozyme. A target cleavage site is selected in the target sequence, and a ribozyme is constructed based on the 5' and 3' nucleotide sequences that flank the cleavage site. Retroviral vectors are engineered to express monomeric and multimeric hammerhead ribozymes targeting the mRNA of EGFH2 polynucleotide coding sequence. These monomeric and multimeric ribozymes are tested in vitro for an ability to cleave the EGFH2 mRNA. A cell line is stably transduced with the retroviral vectors expressing the ribozymes, and the transduction is confirmed by Northern blot analysis and reverse-transcription polymerase chain reaction (RT-PCR). The cells are screened for inactivation of the target mRNA by such indicators as reduction of expression of disease markers or reduction of the gene product of the target mRNA.

The present invention also relates to antisense oligonucleotides designed to interfere with the normal function of EGFH2 polynucleotides. Any modifications or variations of the antisense molecule which are known in the art to be broadly applicable to antisense technology are included within the scope of the invention. Such modifications include preparation of phosphorus-containing linkages as disclosed in U.S. Pat. Nos. 5,536,821; 5,541,306; 5,550,111; 5,563,253; 5,571,799; 5,587,361, 5,625,050 and 5,958,773.

The antisense compounds of the invention can include modified bases as disclosed in U.S. Pat. No. 5,958,773 and patents disclosed therein. The antisense oligonucleotides of the invention can also be modified by chemically linking the oligonucleotide to one or more moieties or conjugates to enhance the activity, cellular distribution, or cellular uptake of the antisense oligonucleotide. Such moieties or conjugates include lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773.

Chimeric antisense oligonucleotides are also within the scope of the invention, and can be prepared from the present inventive oligonucleotides using the methods described in, for example, U.S. Pat. Nos. 5,013,830, 5,149,797, 5,403,711, 5,491,133, 5,565,350, 5,652,355, 5,700,922 and 5,958,773.

In the antisense art a certain degree of routine experimentation is required to select optimal antisense molecules for particular targets. To be effective, the antisense molecule preferably is targeted to an accessible, or exposed, portion of the target RNA molecule. Although in some cases information is available about the structure of target mRNA molecules, the current approach to inhibition using antisense is via experimentation. mRNA levels in the cell can be measured routinely in treated and control cells by reverse transcription of the mRNA and assaying the cDNA levels. The biological effect can be determined routinely by measuring cell growth or viability as is known in the art.

Measuring the specificity of antisense activity by assaying and analyzing cDNA levels is an art-recognized method of validating antisense results. For example, RNA from treated and control cells can be reverse-transcribed and the resulting cDNA populations analyzed. (Branch, A. D., *T.I.B.S.* 23:45-50, 1998.).

Antisense nucleic acids are designed to specifically bind to RNA, resulting in the formation of RNA-DNA or RNA-RNA hybrids, with an arrest of DNA replication, reverse transcription or messenger RNA translation. Antisense polynucleotides based on a selected sequence can interfere with expression of the corresponding gene. Antisense polynucleotides are typically generated within the cell by expression from antisense constructs that contain the antisense strand as the transcribed strand. Antisense polynucleotides will bind and/or interfere with the translation of the corresponding mRNA. The expression products of control cells and cells treated with the antisense construct are compared to detect the protein product of the gene corresponding to the polynucleotide. The protein is isolated and identified using routine biochemical methods.

Antisense therapy for a variety of cancers is in clinical phase and has been discussed extensively in the literature. Given the extensive background literature and clinical experience in antisense therapy, one skilled in the art can use antisense EGFH2 polynucleotides as therapeutics. The dosage and means of administration are determined based on the specific qualities of the composition, the patient, the progression of the disease and other relevant factors. Preferably, the therapeutic antisense composition contains an expression construct comprising a promoter upstream of a polynucleotide segment of at least 12, 22, 25, 30, or 35 contiguous nucleotides of EGFH2 in the antisense orientation. Therapeutic antisense agents may be administered locally or systemically by a variety of methods known in the art. Examples cited include those mentioned above and receptor-mediated targeted delivery.

Therapeutic compositions containing antisense EGFH2 polynucleotides are administered in a range of about 100 ng to about 200 mg of polynucleotides for local administration in a gene therapy protocol, as discussed later. In all cases, routine experimentation in clinical trials will determine specific ranges for optimal therapeutic effects.

Polypeptide compositions can also include antibodies and peptides. The effective dosages for therapeutic compositions containing protein, polypeptide or antibody are in the range of about 5 µg to about 50 µg/kg of patient body weight, about 50 µg to about 5 mg/kg, about 100 µg to about 500 µg/kg of patient body weight, and about 200 to about 250 µg/kg.

Antibodies may be polyclonal, monoclonal or single-chain antibodies prepared by methods known in the field. Antibodies specific to polypeptides encoded by EGFH2 bind the protein and inhibit the protein from functioning in the cell. For example, the antibodies can prevent EGFH2 from binding protein partners or receptors. Such antibodies can also induce conformation changes in the polypeptides they bind. The invention also pertains to antibodies directed against protein partners and receptors for EGFH2 polypeptides. Such antibodies can disrupt protein:protein interactions required for cellular function of EGFH2. They can also inhibit downstream signaling by the receptor protein.

Therapeutic compositions and methods comprising peptide agonists and antagonists are also included in the invention. The peptides can affect the function of polypeptides encoded by EGFH2 or their binding partners and receptors.

For example, the peptides may block protein:protein interactions or cause conformational changes which diminish or enhance EGFH2's normal functional activity. The peptides may also alter EGFH2's activity or specificity in a therapeutically useful manner.

The therapeutic polynucleotides and polypeptides of the present invention may be utilized in gene delivery vehicles. The gene delivery vehicle may be of viral or non-viral origin (see generally, Jolly, Cancer Gene Therapy (1994) 1:51-64; Kimura, Human Gene Therapy (1994) 5:845-852; Connelly, Human Gene Therapy (1995) 1:185-193; and Kaplitt, Nature Genetics (1994) 6:148-153). Gene therapy vehicles for delivery of constructs including a coding sequence of EGFH2 can be administered either locally or systemically. These constructs can utilize viral or non-viral vector approaches. Expression of such coding sequences can be induced using endogenous mammalian or heterologous promoters. Expression of the coding sequence can be either constitutive or regulated.

Any gene delivery method known in the art can be utilized. For example, the present invention can employ recombinant retroviruses which are constructed to carry or express a selected nucleic acid molecule of interest. The present invention also employs alphavirus-based vectors and parvoviruses, that can function as gene delivery vehicles. Other gene delivery vehicles and methods may be employed, including polycationic condensed DNA linked or unlinked to killed adenovirus alone, for example Curiel, Hum. Gene Ther. (1992) 3:147-154; ligand linked DNA, for example see Wu, J. Biol. Chem. (1989) 264:16985-16987; eukaryotic cell delivery vehicles, for example see U.S. Ser. No. 08/240,030, filed May 9, 1994, and U.S. Ser. No. 08/404,796; deposition of photopolymerized hydrogel materials; hand-held gene transfer particle gun, as described in U.S. Pat. No. 5,149,655; ionizing radiation as described in U.S. Pat. No. 5,206,152 and in WO92/11033; nucleic charge neutralization or fusion with cell membranes. Additional approaches are described in Philip, Mol. Cell. Biol. (1994) 14:2411-2418, and in Woffendin, Proc. Natl. Acad. Sci. (1994) 91:11581-11585. Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles.

Non-viral delivery methods include, but are not limited to, mechanical delivery systems such as the approach described in Woffendin et al., Proc. Natl. Acad. Sci. USA (1994) 91(24): 11581-11585 and naked DNA protocols. Exemplary naked DNA introduction methods are described in WO 90/11092 and U.S. Pat. No. 5,580,859.

Members of the EGF signaling network are involved in human cancers. For example, some epithelial carcinomas overexpress ErbB-2 at levels 100-fold greater than normal, and in some types of cancers, the extent of overexpression predicts disease outcome and response to treatment (discussed in Burden and Yarden, Neuron 18:847-855 (1997)). The HER-2/neu oncogene encodes a member of the ErbB/HER receptor family which is overexpressed in breast cancers. HER-2/neu expression levels are used as a diagnostic and prognostic factor in diagnosing and predicting response to therapy (reviewed in Ross and Fletcher, Oncologist 3:237-252 (1998)).

Subgenomic EGFH2 polynucleotides and complements thereof can be used as markers to diagnose and determine the prognosis of cancer, tumor progression, hyperproliferative cell growth or accompanying biological and physical manifestations. Levels of EGFH2 polynucleotides or polypeptides in a sample are compared to the levels in a normal control sample. The normal sample can include a pool of cells from a particular tissue or tissues and/or cells from throughout the body. Immunoassays or nucleic acid assays can be used for such measurements. Any observed difference between the sample and normal control can indicate the occurrence of disease or disorder. Typically, if the levels of EGFH2 polynucleotides or polypeptides are higher than those found in the normal control, the results indicate the occurrence of cancer, tumor progression, hyperproliferative cell growth and/or accompanying biological or physical manifestations.

Nucleic acid assays utilize subgenomic polynucleotides capable of hybridizing under stringent conditions to EGFH2 polynucleotides or complements thereof. Polynucleotide probes comprising at least 10 contiguous nucleotides selected from the nucleotide sequence of EGFH2 are labeled, for example, with a radioactive, fluorescent, biotinylated, or chemiluminescent label, and detected by well known methods appropriate for the particular label selected. Subgenomic polynucleotides are preferably intron-free. Polynucleotides corresponding to EGFH2 can be introduced into vectors and propagated in suitable hosts. Plasmids can be introduced into host cells using techniques available in the art. These techniques include, but are not limited to, electroporation and calcium phosphate-mediated transfection. They can be isolated and purified from DNA vectors by standard techniques, such as restriction enzyme digestion and gel electrophoresis or chromatography. The polynucleotides can also be produced using the polymerase chain reaction according to techniques well known in the art.

The subgenomic polynucleotides can be used to compare related genes in normal control tissue and suspected diseased tissue by any means known in the art. For example, the EGFH2 from a suspected diseased tissue can be sequenced and compared with the EGFH2 sequence in the normal tissue. The polynucleotide-related genes, or portions thereof, in the two tissues are amplified, for example using nucleotide primers based on the nucleotide sequence of EGFH2, using the polymerase chain reaction. The amplified genes or portions of genes are hybridized to nucleotide probes selected from the same nucleotide sequence and sequenced. A difference in the nucleotide sequence of the polynucleotide-related gene in the tissue suspected of being diseased compared with the normal nucleotide sequence suggests a role of the polynucleotide-encoded proteins in the disease, and provides a lead for preparing a therapeutic agent. The nucleotide probes or nucleotides incorporated during sequencing are labeled by a variety of methods, such as radiolabeling, biotinylation, or labeling with fluorescent or chemiluminescent tags, and detected by standard methods known in the art.

Alternatively, EGFH2 mRNA levels in normal and suspected diseased tissues are compared. PolyA$^+$ RNA is isolated from the two tissues as is known in the art. For example, one of skill in the art can readily determine differences in the size or amount of polynucleotide-related mRNA transcripts between the two tissues by Northern blot analysis, primer extension, S1 nuclease protection, reverse transcription-polymerase chain reaction (RT-PCR), or in situ hybridization using polynucleotide probes corresponding to EGFH2 or complement thereof. Increased or decreased expression of a polynucleotide-related mRNA in a tissue sample suspected of being diseased, compared with the expression of the same polynucleotide-related mRNA in a normal tissue, suggests that the expressed protein has a role in the disease, and also provides a lead for preparing a therapeutic agent.

EGFH2 gene expression can also be examined using polynucleotide arrays. Polynucleotide arrays provide a high throughput technique that can assay a large number of polynucleotide sequences in a sample. This technology can be used as a diagnostic and as a tool to test for differential expression of an encoded protein. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. No. 5,593,839; U.S. Pat. No. 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734, which are incorporated by reference.

Antibodies which bind EGFH2 and/or variant polypeptides can be used in diagnosing and determining the prognosis of cancer, tumor progression, hyperproliferative cell growth or accompanying biological and physical manifestations. These antibodies may be monoclonal, polyclonal or single chain antibodies and are produced by methods well known in the art.

Any method known in the art can be used to compare EGFH2 encoded proteins from normal control samples and suspected diseased samples. The size of the proteins in the two tissues can be compared, for example, using antibodies against polypeptides encoded by EGFH2 to detect EGFH2 polypeptides by western blot. Alterations in the size of the EGFH2 protein in a tissue suspected of being diseased compared with the level in a normal control sample indicate the protein is abnormal, possibly due to truncation, deletion or altered post-translational modification. Size alterations are indicative that EGFH2 has a role in the disease and provides a lead for preparing a therapeutic agent. Other changes, such as protein expression levels and subcellular localization can also be detected immunologically, for example by using antibodies directed against polypeptides encoded by EGFH2 for western blot or immunofluorescence. A higher or lower level of EGFH2 protein in a tissue suspected of being diseased, or in conditioned media of cells derived from said tissue, compared with the level in a normal control sample is indicative that EGFH2 has a role in the disease and provides another lead for preparing a therapeutic agent. Similarly, changes in subcellular localization of EGFH2 protein also indicates EGFH2 has a role in the disease.

Reagents specific for EGFH2 polynucleotides and polypeptides, such as antibodies and nucleotide probes, can be supplied in a kit for detecting the presence of an expression product in a biological sample. The kit can also contain buffers or labeling components, detection reagents, instructions for using reagents to detect and quantify expression products in biological samples and control normal biological samples. Normal biological samples may be in any form suitable for the particular method of detection utilized by the kit. For example, normal biological samples can be polynucleotides, polypeptides, cellular extracts or tissue sections.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLES

Example 1

Identification of EGFH2

A clone derived from a mouse liver cDNA library contained a putative murine EGFH2 (mEGFH2). Sequencing of the mEGFH2 clone revealed that it contains a full length cDNA encoding a predicted 115 amino acid protein. An in-frame stop codon was identified upstream of the initiator ATG.

Cloned mEGFH2 was used to identify a human homolog of the mouse EGFH2 gene. The sequence of the human clone contained 100 bp of unspliced intron sequence. The predicted open reading frame of the human EGFH2 clone (hEGFH2) encodes a 115 amino acid protein. Comparison of the mEGFH2 and hEGFH2 sequences revealed that the proteins are 76% identical (FIG. 1).

EGFH2 does not appear to contain a predicted signal peptide or an Ig domain. However, hydropathy analysis of the mEGFH2 protein revealed a potential transmembrane domain corresponding to an EGF-like domain in the N-terminus of EGFH2 (amino acids 4-50). The mEGFH2 EGF-like domain is 32% identical to the EGF-like domain of neuregulin-1β. Notably, both mEGFH2 and hEGFH2 contain six conserved cysteine residues characteristic of EGF-like proteins. Furthermore, the predicted EGFH2 amino acid sequence contains a putative proteolytic cleavage site C-terminal to the EGF-like domain. Thus, the EGFH2 proteins are members of the EGF family.

Example 2 mRNA Expression

Northern blot analysis of mouse tissues revealed that mEGFH2 is mainly expressed in liver tissue. Two predominant bands of 1.35 kb and 2.4 kb, and three minor bands of 4.0 kb, 4.4 kb and 8 kb, were observed. In addition, mouse heart, lung, skeletal muscle and kidney showed some expression of the 1.35 kb and 2.4 kb mRNAs. Northern blot analysis of various human tissues using a mouse EGFH2 probe identified a similar banding pattern in human skeletal muscle and pancreas tissues.

In situ hybridization performed on mouse day 8.5 and 9.5 p.c. embryos using a mEGFH2 probe demonstrated that EGFH2 is widely expressed throughout the embryo except in neural tube and limb areas. Furthermore, specific expression observed in heart tissue became restricted to the atrium of the heart in day 11.5 embryos. EGFH2 thus displays both tissue-specific and developmental stage-specific expression in mammals. Additionally, in situ hybridization of human pancreatic samples using a mEGFH2 probe revealed higher levels of EGFH2 expression in a human pancreatic tumor sample as compared to normal pancreatic tissue, indicating that EGFH2 has increased expression in cancerous pancreatic cells.

Example 3

Biological Properties

Secretion:
Precursor forms of the EGF family are proteolytically processed to yield a secreted growth factor. To demonstrate that EGFH2 is secreted, a construct containing mEGFH2 with an HA tag at its C-terminus was cloned into the pCS2 expression vector and transfected into Cos cells. Supernatant of the transfected Cos cells and cell lysates were analyzed by western blot using an HA antibody. A protein of approximately 20 kD was detected in cell lysates, but not in Cos cell supernatant. However, it is likely that a secreted form of EGFH2 cannot be detected after proteolytic processing, since a putative proteolytic cleavage site is located C-terminal of the predicted secreted product containing the EGF-like domain, and the HA tag is located at the C-terminus of the precursor protein.

To further examine whether EGFH2 is secreted, Cos cells transfected with the HA-tagged mEGFH2 expression construct or a vector control are radiolabeled with [$^{35}$S]-methionine. The cell lysates and supernatants are resolved by SDS-PAGE and the presence of EGFH2 polypeptides is determined by autoradiography. The presence of a novel radiolabeled band in the cell supernatant indicates that EGFH2 is secreted. The cell lysates and supernatants are also examined by western blot or immunoprecipitation of EGFH2 polypeptides using antibodies directed against N-terminal regions of the EGFH2 precursor protein. The presence of immunoprecipitating or western blotting polypeptides specific to HA-tagged EGFH2 transfected cells in the cell supernatant indicates that EGFH2 is secreted.

Mitogenic Properties:

Members of the neuregulin family have mitogenic effects on cell proliferation. To determine that EGFH2 has mitogenic properties, the effect of EGFH2 sense and antisense RNA on germinal vesicle breakdown (GVBD) was examined. EGFH2 cDNA insert was cloned into the pCDNA3 vector in the opposite direction to the CMV promoter. Sense (sample #3) and antisense (sample #2) mRNA of EGFH2 were prepared from the EGFH2 gene in pCDNA3 and sense (sample #4) mRNA of EGFH2 with an HA tag was prepared from the EGFH2 gene in the pCS2 vector by in vitro transcription. Each mRNA sample was injected into *Xenopus* oocytes to evaluate their effect on GVBD. The results are tabulated in FIG. 4. EGFH2 induces meiotic maturation of *Xenopus oocytes*.

The mitogenic activities of neuregulin family members can be mediated by the MAP kinase pathway. To confirm that EGFH2 induces meiotic maturation of *Xenopus* oocytes by activating the MAP kinase pathway, the ability of EGFH2 to induce GVBD is examined in the presence of dominant negative Raf or dominant negative MAP kinase. Sense or antisense EGFH2 mRNA is injected into *Xenopus* oocytes in the presence or absence of various amounts of sense or antisense dominant negative Raf or dominant negative Map kinase. The effect of the various mRNA combinations on GVBD is measured.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. An isolated polypeptide consisting of amino acids selected from the group consisting of:
   (a) amino acids from 1 to 115 of SEQ ID NO:4; and
   (b) amino acids from 2 to 115 of SEQ ID NO:4;
   said polypeptide having mitogenic activity as determined by *Xenopus oocyte* maturation assay.

2. An analog of an isolated polypeptide that has mitogenic activity as determined by *Xenopus oocyte* maturation assay, wherein said polypeptide has an amino acid sequence selected from the group consisting of
   (a) amino acids from about 1 to about 115 of SEQ ID NO:4, and
   (b) amino acids from about 2 to about 115 of SEQ ID NO:4;
   and wherein said analog is identical to said amino acid sequence selected from the group consisting of (a) and (b) except for having at least one conservative amino acid substitution selected from the group consisting of Arg to Lys; Glu to Asp; Tyr to Phe; Leu to Met; and Val to Ile.

3. An isolated polypeptide comprising amino acids selected from the group consisting of:
   (a) amino acids from 1 to 115 of SEQ ID NO:4; and
   (b) amino acids from about 2 to about 115 of SEQ ID NO:4.

4. An epitope-bearing portion of a polypeptide of SEQ ID NO:4 which consists of between about 10 and 100 contiguous amino acids of SEQ ID NO:4.

5. The epitope-bearing portion of claim 4, which consists of between about 12 and 50 contiguous amino acids of SEQ ID NO:4.

6. The epitope-bearing portion of claim 4, which consists of between about 15 and 25 contiguous amino acids of SEQ ID NO:4.

7. The isolated polypeptide of any one of claims 1-3, wherein the polypeptide is a human polypeptide.

8. The isolated polypeptide of claim 2, wherein the polypeptide shares the same expression pattern as a polypeptide comprising SEQ ID NO:4.

9. An isolated polypeptide comprising amino acids 1 to amino acid 115 of SEQ ID NO:4.

10. An isolated polypeptide comprising amino acids 2 to amino acid 115 of SEQ ID NO:4.

11. An analog of an isolated polypeptide comprising amino acids 1 to amino acid 115 of SEQ ID NO:4, wherein said analog has mitogenic activity as determined by *Xenopus oocyte* maturation assay, and wherein said analog is identical to amino acids 1 to amino acid 115 of SEQ ID NO:4 except for comprising at least one conservative amino acid change selected from the group consisting of Arg to Lys; Glu to Asp; Tyr to Phe; Leu to Met; and Val to Ile.

12. An analog of an isolated polypeptide comprising amino acids 2 to amino acid 115 of SEQ ID NO:4, wherein said polypeptide has mitogenic activity as determined by *Xenopus oocyte* maturation assay, and wherein said analog is identical to amino acids 2 to amino acid 115 of SEQ ID NO:4 except for comprising at least one conservative amino acid change selected from the group consisting of Arg to Lys; Glu to Asp; Tyr to Phe; Leu to Met; and Val to Ile.

* * * * *

SEQUENCE LISTING

<160> NUMBER OF SEQ ID NOS: 7

<210> SEQ ID NO 1
<211> LENGTH: 348
<212> TYPE: DNA
<213> ORGANISM: Mus musculus

<400> SEQUENCE: 1

```
atgccaacag atcacgagca gccctgtggt cccaggcaca ggtcattttg cctcaatggg      60
gggatttgtt atgtgatccc tactatcccc agcccattct gtaggtgcat tgaaaattac     120
accggagcac gctgcgaaga ggttttctc ccaagctcca gcatcccaag cgaaagtaat     180
ctgtcggcag ctttcgtggt gctggcggtc ctcctcactc ttaccatcgc ggcgctctgc     240
ttcctgtgca ggaagggcca ccttcagagg gccagttcag tccagtgtga gatcagcctg     300
gtagagacaa acaataccag aacccgtcac agccacagag aacactga                  348
```

<210> SEQ ID NO 2
<211> LENGTH: 115
<212> TYPE: PRT
<213> ORGANISM: Mus musculus

<400> SEQUENCE: 2

```
Met Pro Thr Asp His Glu Gln Pro Cys Gly Pro Arg His Arg Ser Phe
 1               5                  10                  15

Cys Leu Asn Gly Gly Ile Cys Tyr Val Ile Pro Thr Ile Pro Ser Pro
            20                  25                  30

Phe Cys Arg Cys Ile Glu Asn Tyr Thr Gly Ala Arg Cys Glu Glu Val
        35                  40                  45
```

```
Phe Leu Pro Ser Ser Ile Pro Ser Glu Ser Asn Leu Ser Ala Ala
    50              55                  60

Phe Val Leu Ala Val Leu Leu Thr Leu Thr Ile Ala Ala Leu Cys
65              70              75                      80

Phe Leu Cys Arg Lys Gly His Leu Gln Arg Ala Ser Ser Val Gln Cys
                85              90                      95

Glu Ile Ser Leu Val Glu Thr Asn Asn Thr Arg Thr Arg His Ser His
                100             105             110

Arg Glu His
        115
```

<210> SEQ ID NO 3
<211> LENGTH: 348
<212> TYPE: DNA
<213> ORGANISM: Homo sapiens

<400> SEQUENCE: 3

```
atgccaacag atcacgaaga gccctgtggt cccagtcaca agtcgttttg cctgaatggg    60
gggctttgtt atgtgatacc tactattccc agcccatttt gtaggtgcgt tgaaaactat   120
acaggagctc gttgtgaaga ggttttctc ccaggctcca gcatccaaac taaaagtaac   180
ctgtttgaag cttttgtggc attggcggtc ctagtaacac ttatcattgg agccttctac   240
ttcctttgca ggaaaggcca ctttcagaga gccagttcag tccagtatga tatcaacctg   300
gtagagacga gcagtaccag tgccaccac agtcatgaac aacactga                348
```

<210> SEQ ID NO 4
<211> LENGTH: 115
<212> TYPE: PRT
<213> ORGANISM: Homo sapiens

<400> SEQUENCE: 4

```
Met Pro Thr Asp His Glu Glu Pro Cys Gly Pro Ser His Lys Ser Phe
1               5                   10                  15

Cys Leu Asn Gly Gly Leu Cys Tyr Val Ile Pro Thr Ile Pro Ser Pro
                20                  25                  30

Phe Cys Arg Cys Val Glu Asn Tyr Thr Gly Ala Arg Cys Glu Glu Val
            35                  40                  45

Phe Leu Pro Gly Ser Ser Ile Gln Thr Lys Ser Asn Leu Phe Glu Ala
    50              55                  60

Phe Val Ala Leu Ala Val Leu Val Thr Leu Ile Ile Gly Ala Phe Tyr
65              70              75                      80

Phe Leu Cys Arg Lys Gly His Phe Gln Arg Ala Ser Ser Val Gln Tyr
                85              90                      95

Asp Ile Asn Leu Val Glu Thr Ser Ser Thr Ser Ala His Ser His Ser His
                100             105             110

Glu Gln His
        115
```

<210> SEQ ID NO 5
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 5

```
Glu Gln Lys Leu Ile Ser Glu Glu Asp Leu
1               5                   10
```

```
<210> SEQ ID NO 6
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 6

Leu Val Pro Arg Gly
 1               5

<210> SEQ ID NO 7
<211> LENGTH: 10
<212> TYPE: PRT
<213> ORGANISM: Artificial Sequence
<220> FEATURE:
<223> OTHER INFORMATION: Synthetically generated peptide

<400> SEQUENCE: 7

Ser Ala Trp Arg His Pro Gln Phe Gly Gly
 1               5                  10
```